United States Patent [19]
Yabe et al.

[11] Patent Number: 5,526,928
[45] Date of Patent: Jun. 18, 1996

[54] PACKAGE FOR PACKAGING A PROTECTION COVER WITH CHANNEL FOR ENDOSCOPE

[75] Inventors: Hisao Yabe, Hachioji; Yoshihiro Iida, Tama; Akira Suzuki; Hideo Ito, both of Hachioji; Yoshio Tashiro, Hino; Minoru Yamazaki; Osamu Tamada, both of Hachioji; Ichiro Nakamura, Kokubunji, all of Japan

[73] Assignee: Olympus Optical Co., Ltd., Tokyo, Japan

[21] Appl. No.: 312,954

[22] Filed: Sep. 30, 1994

Related U.S. Application Data

[63] Continuation of Ser. No. 37,408, Mar. 26, 1993, abandoned.

[30] Foreign Application Priority Data

| Jan. 22, 1993 | [JP] | Japan | 5-001364 U |
| Jan. 22, 1993 | [JP] | Japan | 5-001365 U |
| Jan. 22, 1993 | [JP] | Japan | 5-001366 U |
| Jan. 22, 1993 | [JP] | Japan | 5-001367 U |

[51] Int. Cl.⁶ ............................. B65D 83/10
[52] U.S. Cl. ............... 206/364; 206/363; 206/564; 206/438
[58] Field of Search ............... 206/363, 364, 206/365, 564, 438, 439

[56] References Cited

U.S. PATENT DOCUMENTS

| 3,035,691 | 5/1962 | Rasmussen et al. | 206/364 |
| 3,633,758 | 1/1972 | Morse | 206/364 |
| 4,366,901 | 1/1983 | Short | 206/364 |
| 4,646,722 | 3/1987 | Silverstein et al. | |
| 4,715,360 | 12/1987 | Akui et al. | |
| 4,721,097 | 1/1988 | D'Amelio | |
| 4,741,326 | 5/1988 | Sidall et al. | |
| 4,779,727 | 10/1988 | Taterka et al. | 206/364 |
| 4,825,850 | 5/1989 | Opie et al. | |
| 4,858,001 | 8/1989 | Milbank et al. | |
| 4,869,238 | 9/1989 | Opie et al. | |
| 4,877,033 | 10/1989 | Seitz | |
| 4,878,485 | 11/1989 | Adair | |
| 4,947,827 | 8/1990 | Opie et al | |
| 4,991,564 | 2/1991 | Takahashi et al. | |
| 4,991,565 | 2/1991 | Takahashi et al. | |
| 4,997,084 | 3/1991 | Opie et al. | |
| 5,025,778 | 6/1991 | Silverstein et al. | |
| 5,050,585 | 9/1991 | Takahashi | |
| 5,082,112 | 1/1992 | Dunklee | 206/363 |
| 5,105,942 | 4/1992 | van Veen et al. | 206/493 |
| 5,131,537 | 7/1992 | Gonzales | 206/439 |
| 5,198,894 | 3/1993 | Hicks | |
| 5,201,908 | 4/1993 | Jones | |
| 5,217,001 | 6/1993 | Nakao et al. | |
| 5,237,984 | 8/1993 | Williams, III et al. | |
| 5,301,657 | 4/1994 | Lafferty et al. | |
| 5,334,142 | 8/1994 | Paradis | 206/364 |

FOREIGN PATENT DOCUMENTS

| 0341719A1 | 11/1989 | European Pat. Off. |
| 0349479A1 | 1/1990 | European Pat. Off. |
| 4325138 | 11/1992 | Japan |

*Primary Examiner*—David T. Fidei
*Attorney, Agent, or Firm*—Watson Cole; Stevens Davis

[57] ABSTRACT

A package assembly for packaging an endoscope cover for covering the outer surface of the endoscope is disclosed. The package comprises a cover for an insertion tube section of the endoscope, and a package base member for accommodating the endoscope cover therein, the cover section is accommodated in the package base member so as not to overlap itself while being in the state of packaging.

8 Claims, 14 Drawing Sheets

FIG_1
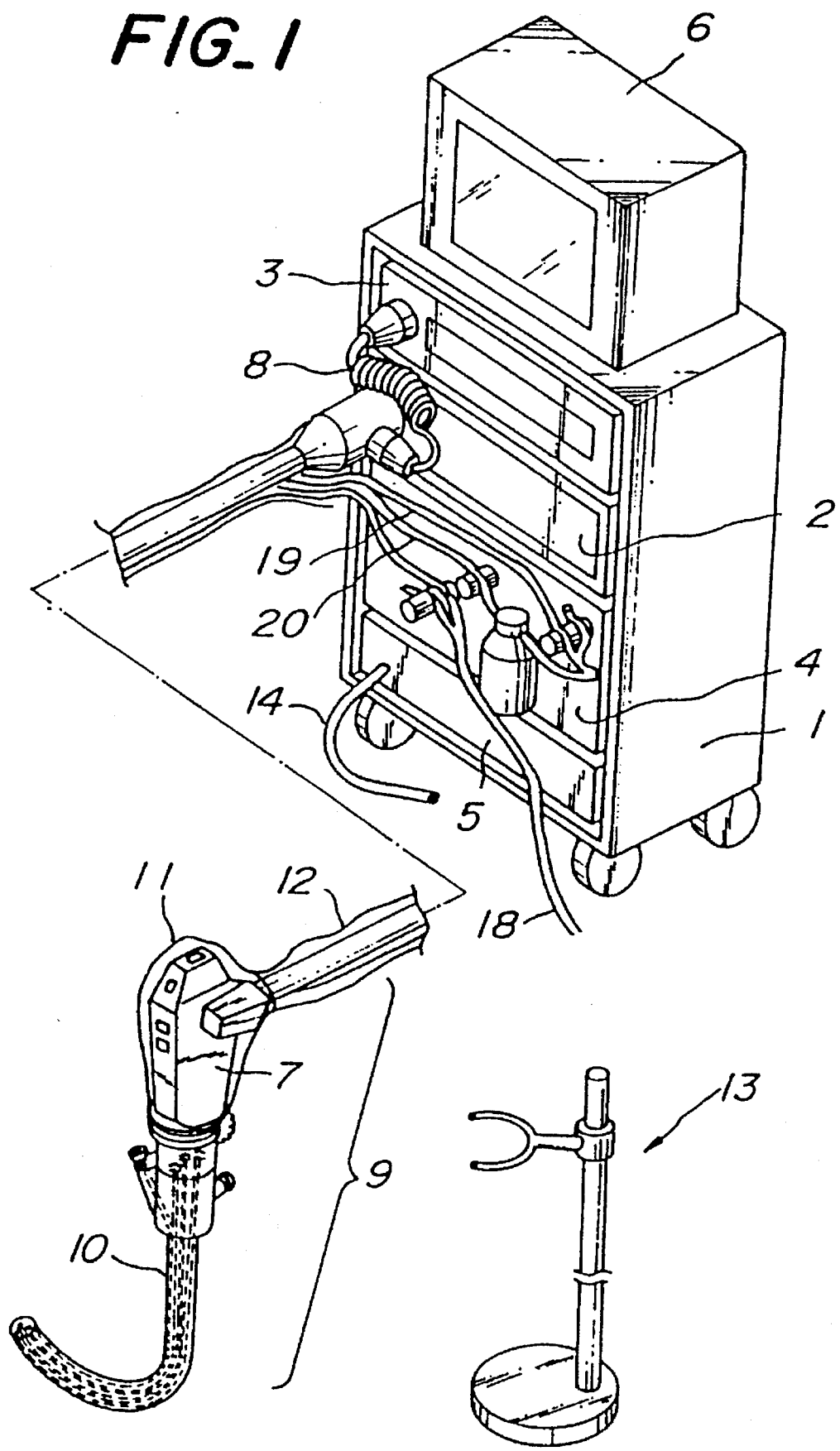

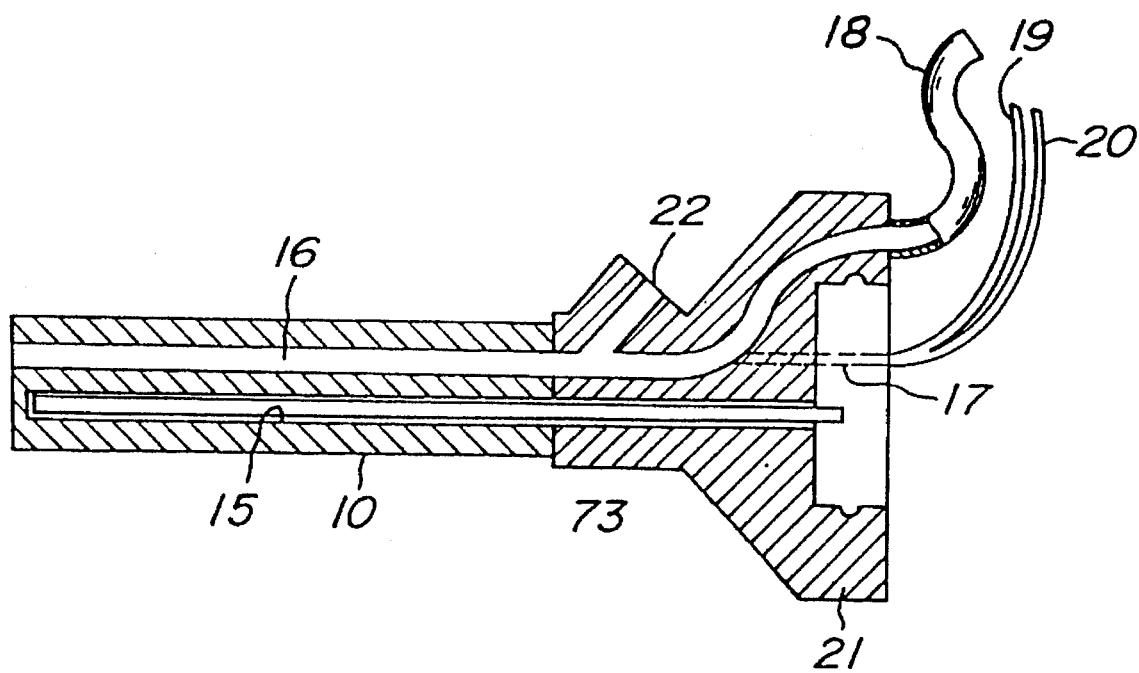
FIG_2
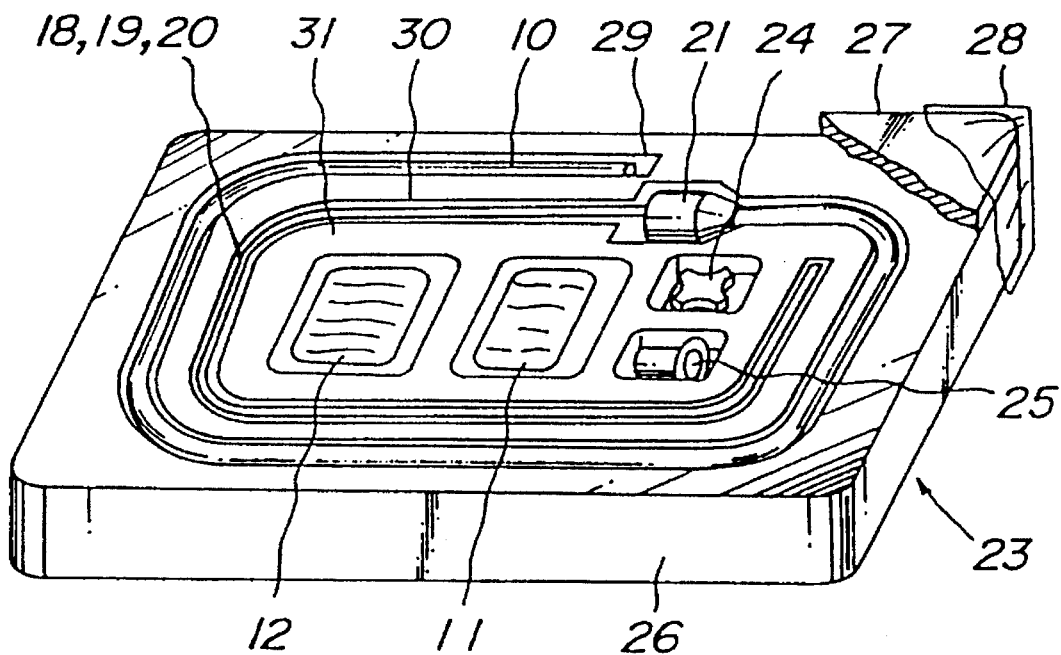
FIG_3

FIG_4
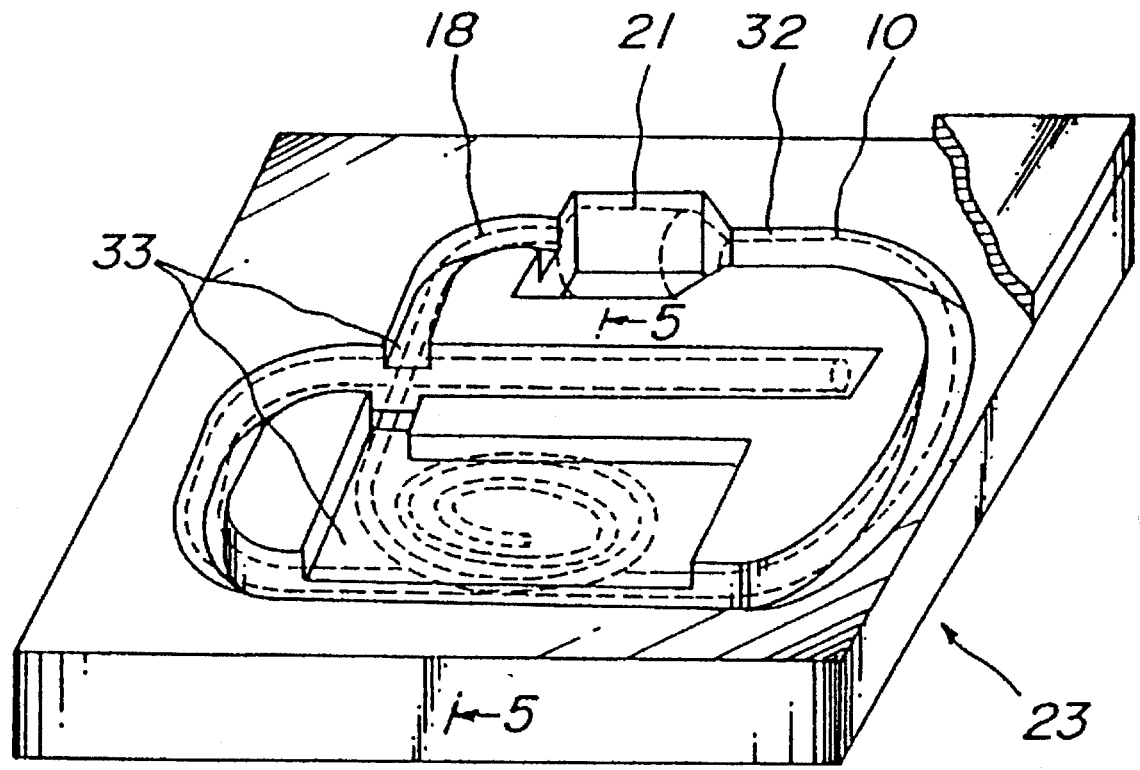

FIG_7a
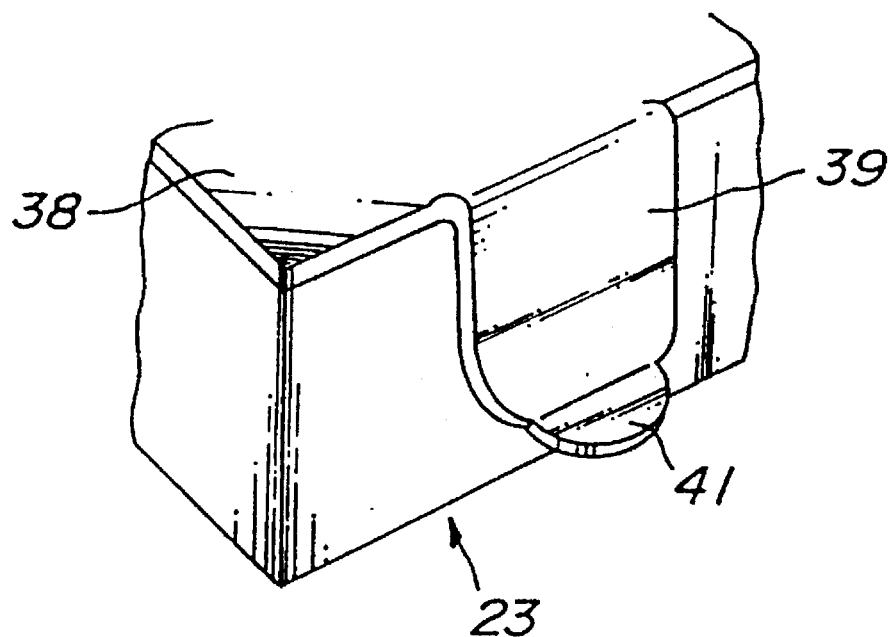
FIG_7b
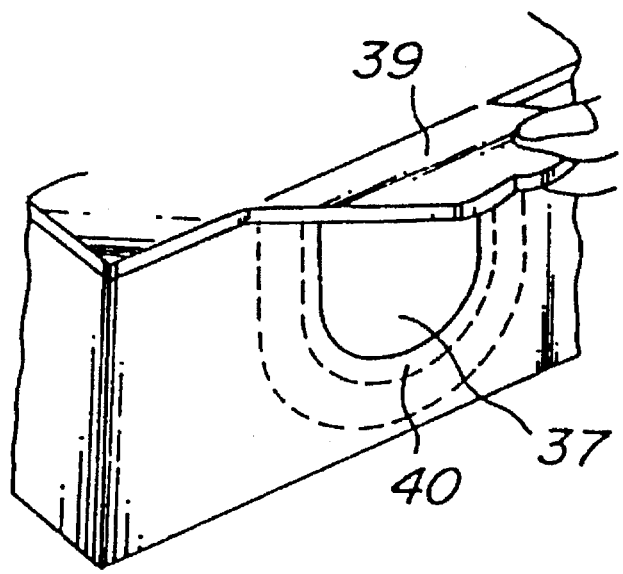

FIG_8
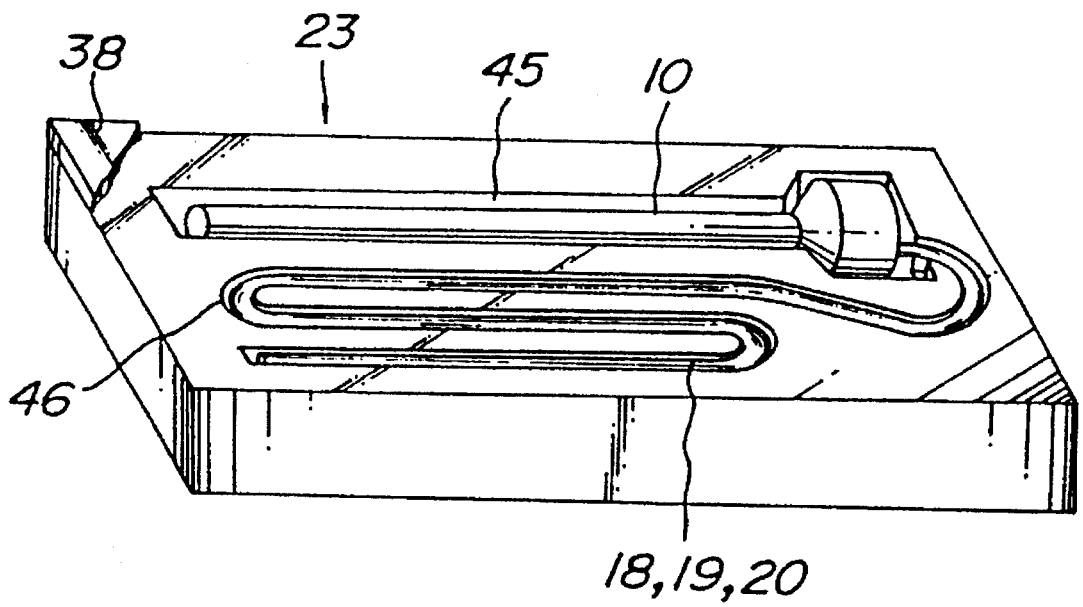
FIG_9
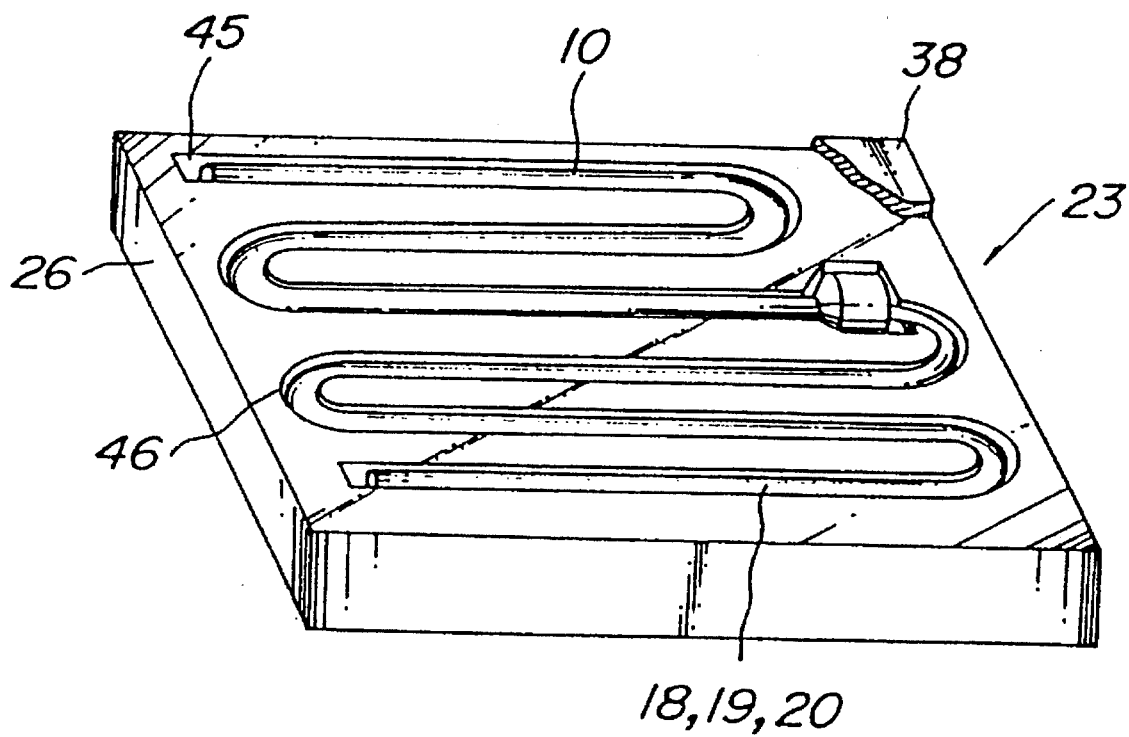

FIG._10a
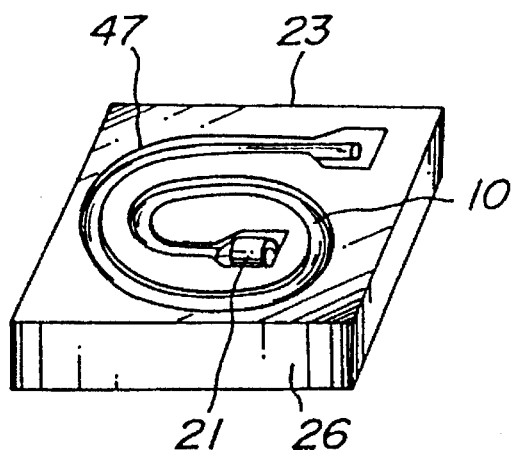
FIG._10b
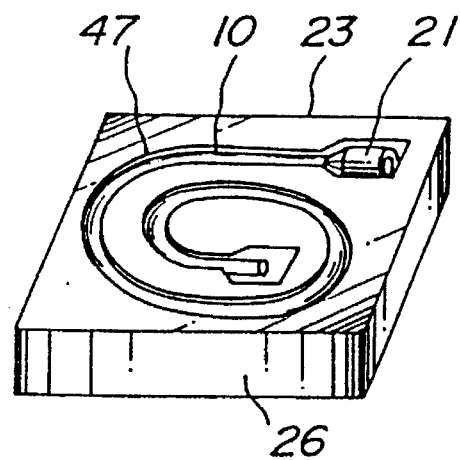
FIG._11
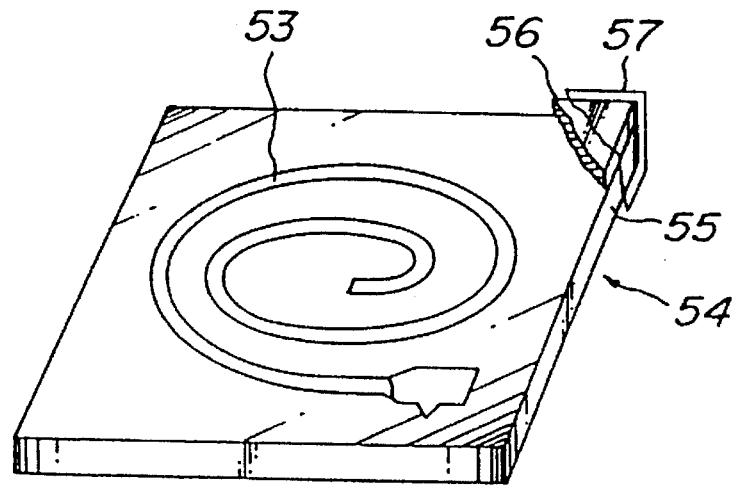

FIG_12
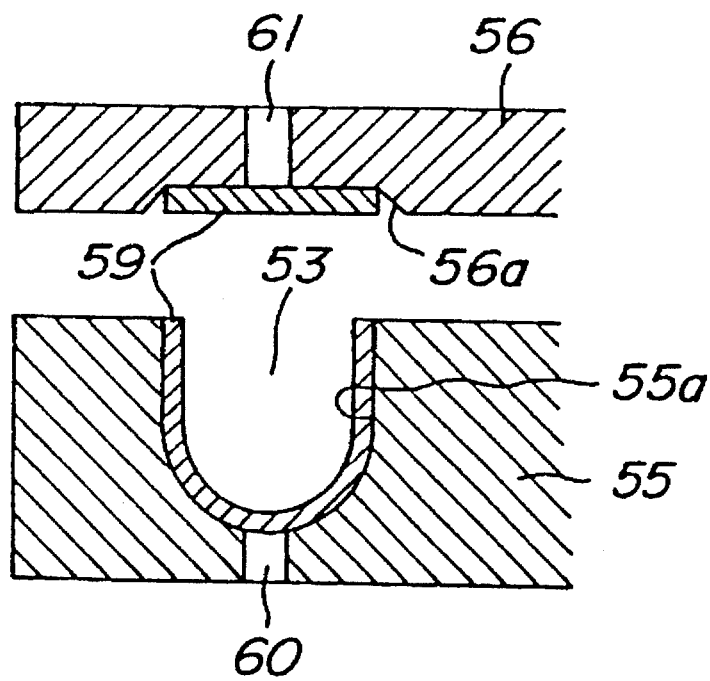
FIG_13a    FIG_13b
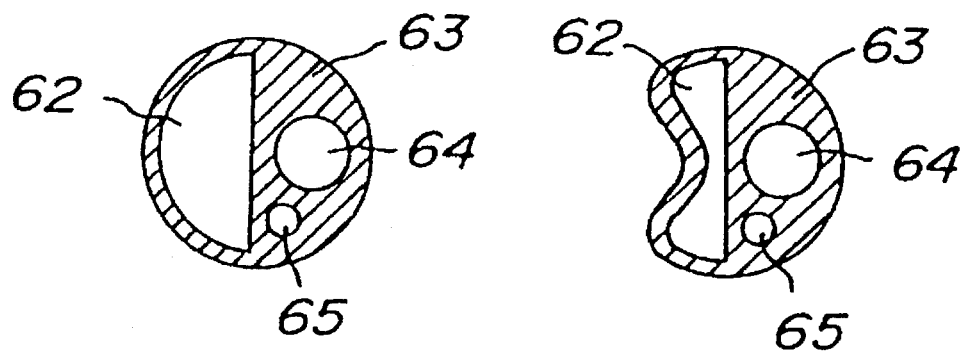

FIG._14
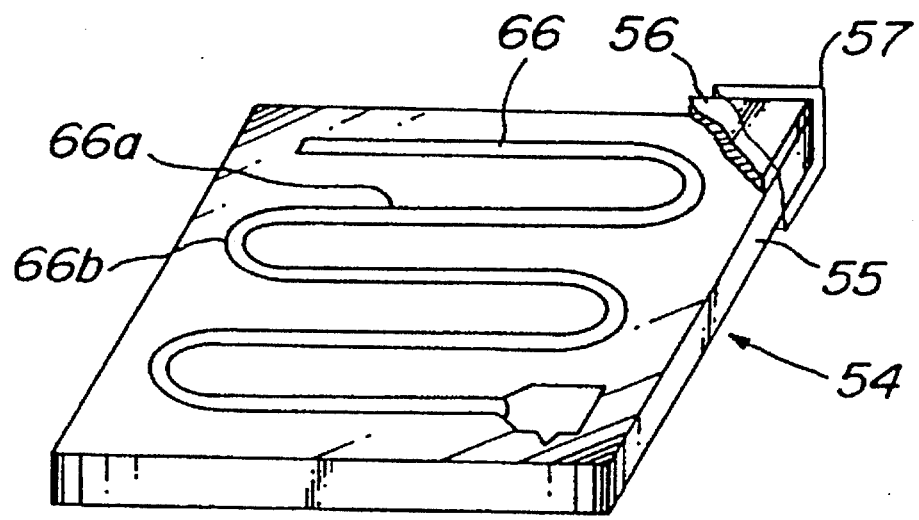
FIG._15
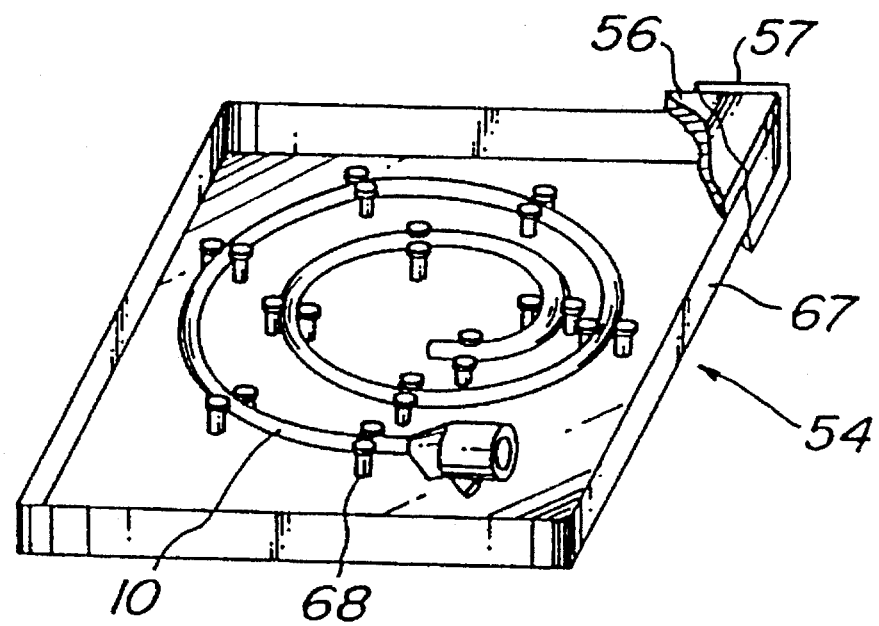

FIG._16
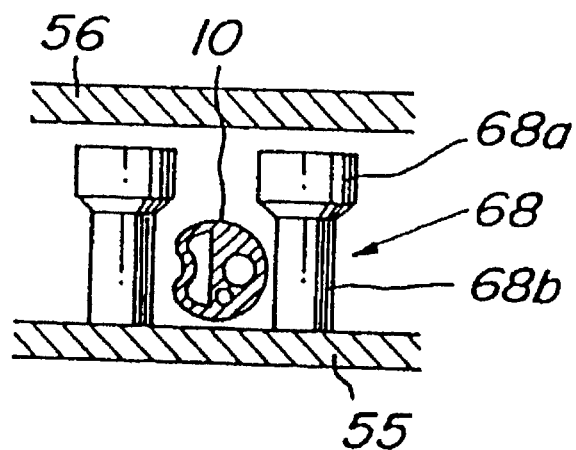
FIG._17
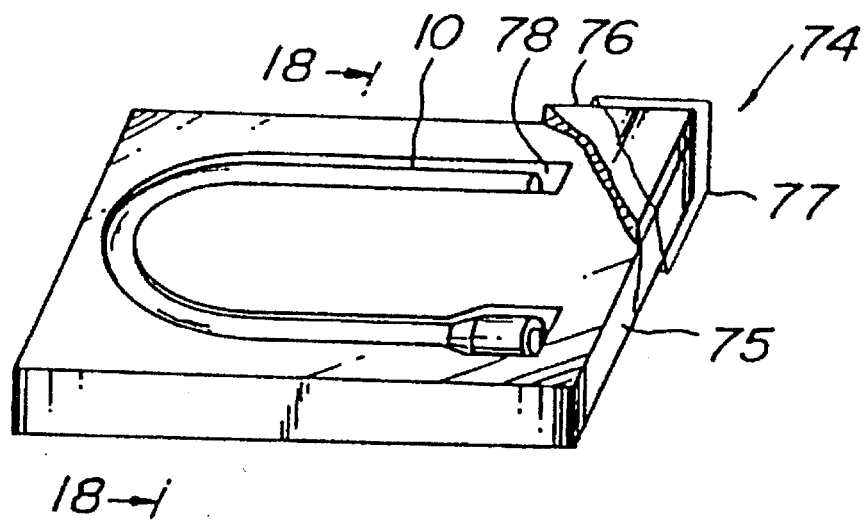

FIG._18
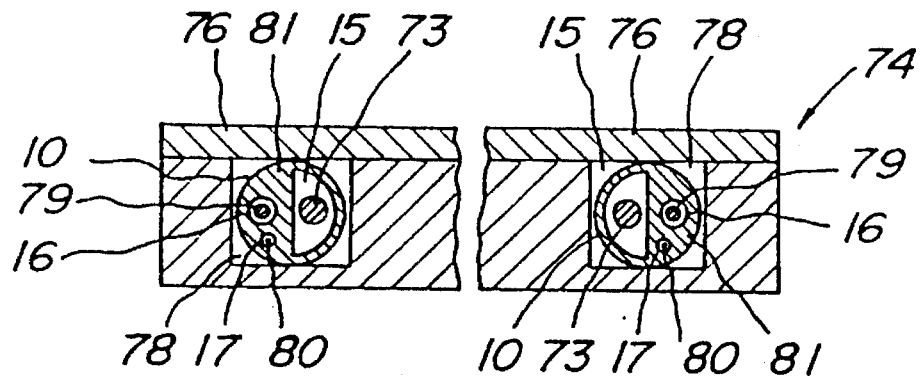
FIG._19
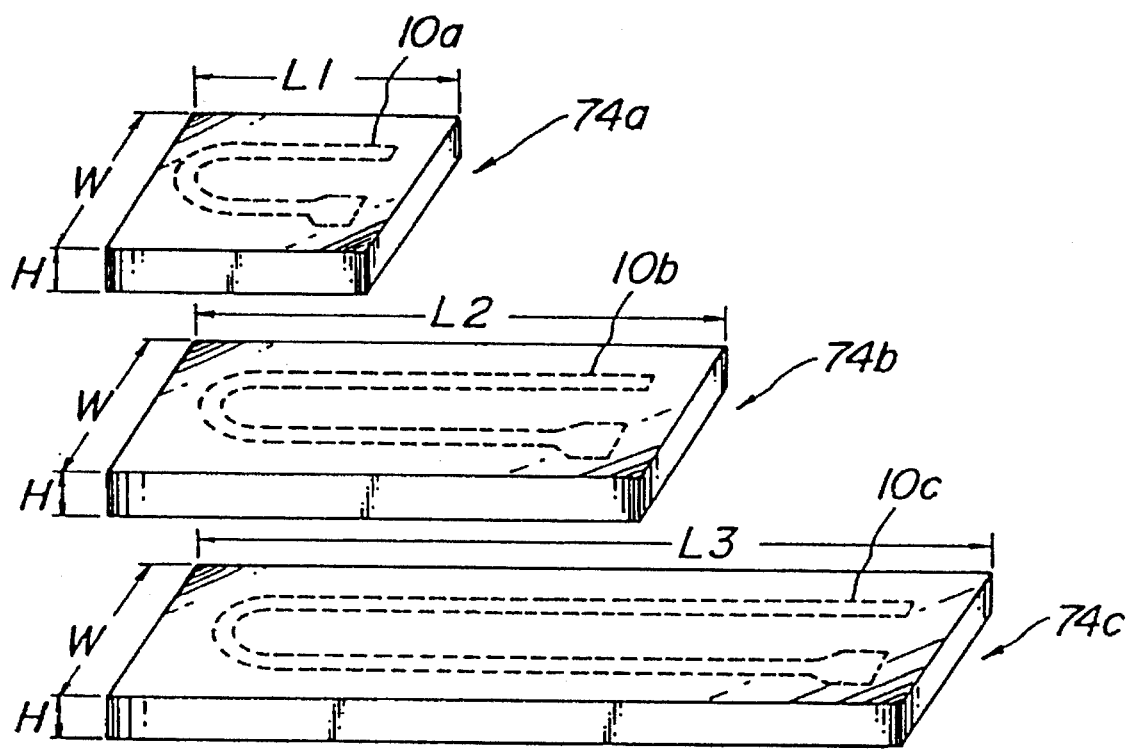

FIG._21
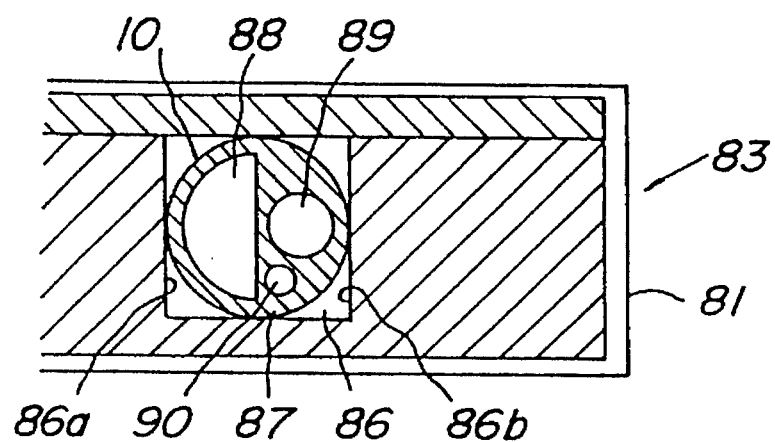
FIG._22
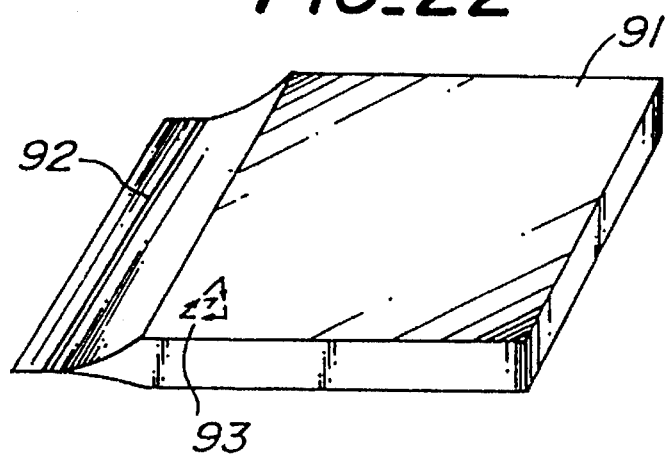
FIG._23
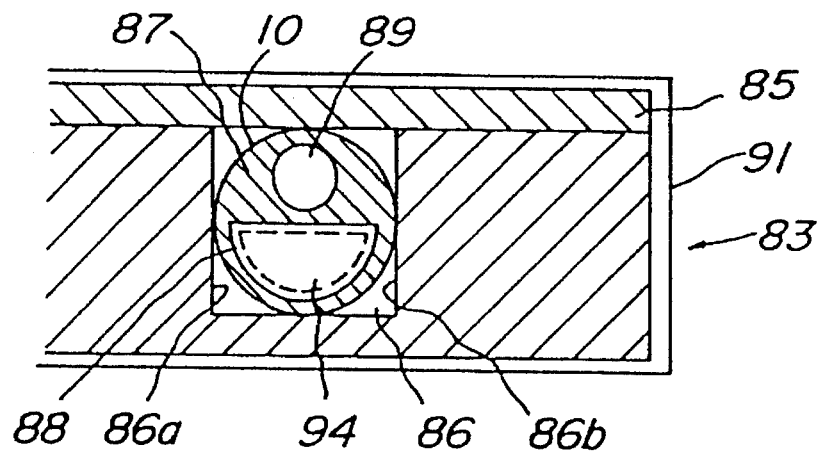

FIG_24
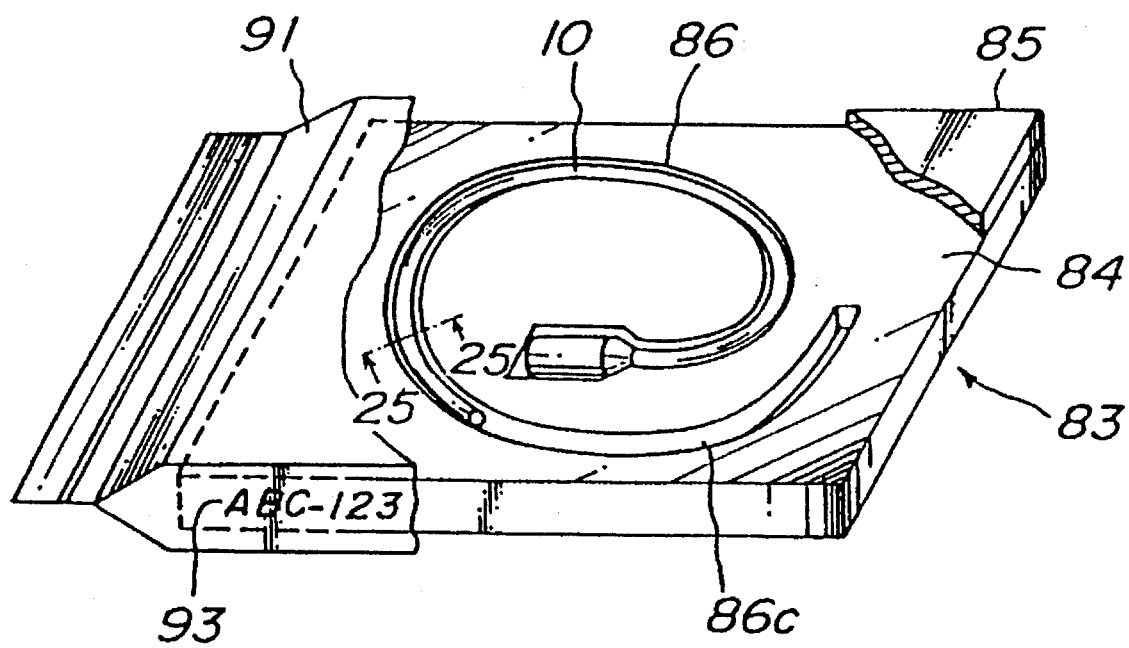
FIG_25
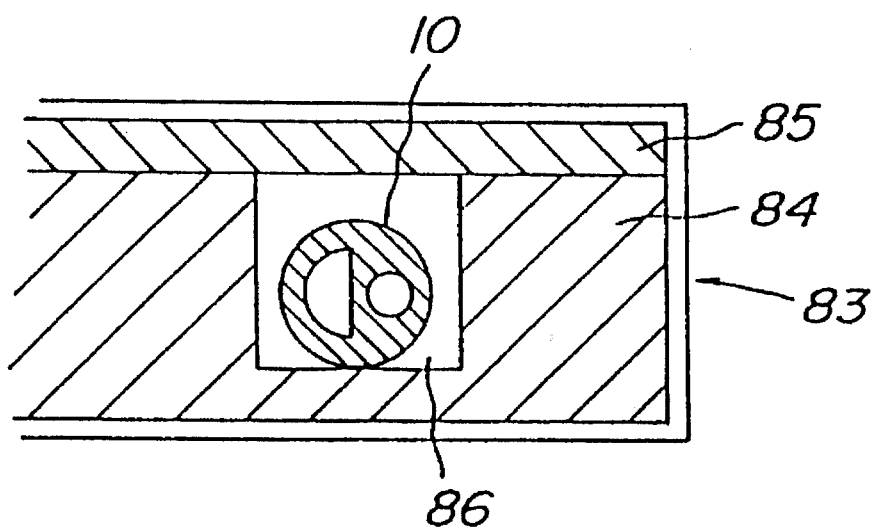

PACKAGE FOR PACKAGING A PROTECTION COVER WITH CHANNEL FOR ENDOSCOPE

This application is a continuation of application Ser. No. 08/037,408, filed Mar. 26, 1993 (abandoned).

BACKGROUND OF THE INVENTION

1. Field of the Invention

The present invention relates to a package for packaging a protection cover with at least one channel for use in an endoscope.

2. Description of the Related Art

An endoscope system has been widely utilized for providing diagnostic and therapeutic indications for coeliac cavities of patients and for inspecting an inside of a mechanical structure. To this end, there have been developed various kinds of endoscopes. For instance, in order to inspect or treat the oesophagus, stomach and duodenum, upper endoscopes have been utilized. Further, colonoscopes have been developed to examine colons and sigmoidoscopes have been proposed to inspect rectums and sigmoid colons. When effecting the endoscopic procedure, an inserting portion of the endoscope has to be inserted into a cavity, so that the outer surface of the insertion section of the endoscope is contaminated. Such a contaminated endoscope could not be successively used for another patients. Therefore, once the endoscope is used to diagnose and/or treat a patient, it is necessary to clean the endoscope. Of course, the cleaning of the endoscope requires a substantial time and during this cleaning time, it is impossible to perform the endoscopic procedure. In order to mitigate such a waiting time, it is necessary to prepare a large number of endoscopes. However, endoscopes are rather expensive, so that it is practically difficult to prepare a large number of endoscopes particularly in a small hospital or clinic. Therefore, in almost all hospitals and clinics, in practice, after the endoscope has been used for examining a patient, the endoscope is immediately cleaned. Typically, this cleaning requires several minutes to ten minutes. In order to effect the complete washing and sterilization, the cleaning has be to performed for several tens of minutes.

Further, the endoscope has various channels such as an air channel, a water channel, a suction channel, a forceps channel which extend along the insertion section from its proximal end to its distal end, and these channel are connected via tubes to respective devices such as an air supply pump, a water supply pump, a water suction pump and an air suction pump. These channels are subjected to contact with living tissues and liquids, so that in order to completely clean these channels, the endoscope cleaning time is liable to be much longer. Then, the endoscope could not be utilized efficiently. In a large hospital or clinics, a large number of endoscopes may be prepared in order to mitigate the problem of cleaning time. However, this solution results in an increase in operating cost. Further, in a small clinic, it is practically impossible to prepare a number of expensive endoscopes.

Moreover, when the endoscope is cleaned, some chemicals are used. The chemicals are toxic and might injure operators. Further, the damage of the environment due to the chemicals has to be avoided as far as possible. This also results in an increase in the operating cost. It should be noted that the endoscope might be broken during the cleaning and the usable time of the endoscope is liable to be shortened by the cleaning.

It is a matter of course that if the endoscope is not cleaned sufficiently, there might be a danger of infection not only for patients, but also for doctors and operators who are brought into contact with the endoscope.

In order to avoid the above explained various problems, it has been proposed to cover the endoscope with a disposable protection sheath having channels formed therein. For instance, U.S. Pat. Nos. 4,721,097, 4,741,326, 4,869,238, 4,991,564, 4,991,565, 5,050,585 disclose various kinds of the protection sheath having at least one channel. In U.S. Pat. No. 4,646,722, there is shown a system in which the endoscope is covered with a protection sheath, while a tube having channels formed therein is inserted into the U-shaped cutout formed in an outer surface of the endoscope along a longitudinal axis thereof. Upon diagnosis, the insertion section of the endoscope is covered with the protection sheath, and after the inspection, the sheath is removed from the insertion section and is then discarded. Therefore, it is no more necessary to clean the endoscope after every the inspection.

In the above mentioned U.S. Patent Specifications, the protection sheath is constructed to cover only the insertion section of the endoscope, but does not cover an operation section of the endoscope. It should noted that the operation section of the endoscope is treated by hands of doctor and operators and thus is brought into contact with the living tissues and liquids of a patient. Therefore, in order to attain a perfect disinfection, it is necessary to cover the operation section of the endoscope. In European Patent Publication No. 0 349 479 A1, there is disclosed an endoscope system, in which not only the insertion section, but also the operation section of the endoscope are covered with a disposable protection cover-like member. That is to say, the protection cover-like member comprises a sheath portion for covering the insertion section of the endoscope and a bag portion for covering the operation section, the sheath portion and bag portion being integrally formed. The operation section of the endoscope is usually provided with various operating members such as angle knobs and optical systems adjusting members. The endoscope shown in the above mentioned European Patent Publication No. 0 349 479 A1 is of a colonoscope type, so that the angle knobs are not provided. However, the focus adjusting ring has to be operated during the inspection. To this end, an aperture is formed in the bag portion of the protection cover-like member at a position corresponding to the focus adjusting ring. In this case, in order to operate the ring easily, it is preferable to form a large aperture. Then, the contamination via the aperture is liable to be large. In order to avoid such a drawback, in European Patent Publication No. 0 341 719 A1, there is proposed another endoscope system, in which an insertion section of an endoscope is covered with a disposable protection bag which is mated or joined with the protection sheath in order to prevent the contamination at the junction of the sheath and the bag. In this known system, the angle knobs are detachably secured to a shaft extending from a housing of the operation section and the shaft is protruded from the protection bag through an aperture formed in the bag. Such a diameter of the shaft is much smaller than a diameter of the angle knobs, a size of the aperture can be made much smaller than the angle knobs. Therefore, a possibility of the contamination via the aperture formed in the bag can be reduced as compared with a case in which a large aperture through which the angle knobs are projected from the bag is formed in the bag.

However, in the usual endoscopes, the angle knobs for moving the distal end of the insertion section in the up and down directions as well as in the right and left directions are secured to the shaft and could not be removed from the shaft during usual usage. Therefore, in the known endoscope, the couplings of the angle knobs with the shaft are effected in various ways, and a set of angle knobs for a certain endoscope could not be secured to a shaft of another endoscope. In the usual endoscope system, this does not cause any problem, because the angle knobs and shaft are not decoupled from each other. However, in the endoscope system disclosed in the above European Patent Publication No. 0 341 719 A1, this results in a serious problem. In an endoscope procedure area, there are arranged various endoscopes of different types, and therefore, once the angle knobs are removed from the shaft extending from the operation section of the endoscope, it is rather difficult to select correct angle knobs. If angle knobs are not forceably mated with the shaft, the angle knobs and/or shaft might be broken.

In the system including the endoscope and the disposable protection sheath, if a pin hole is formed in the sheath, contamination arises via the pin hole. In order to avoid such a problem, respective protection sheath have to be checked in a factory and only sheaths which have no pin hole are shipped or forwarded. However, known sheaths are not formed to effect such a pin hole check easily, so that in practice, the pin hole check has not been performed sufficiently. Therefore, there is a danger that a protection sheath having a pin hole is used for the endoscope procedure. Therefore, just before the usage of the protection sheath, it is preferable to effect the pin hole check at the endoscope procedure site. However, in the known system disclosed in the above mentioned prior art references, this pin hole check could not be carried out easily.

Further, in the known endoscope system using the disposable protection sheath, the various channels are provided within the sheath. In practice, these channels are formed by flexible tubes and these tubes extend within the sheath from a proximal end to a distal end. At these proximal and distal ends, ends of these tubes are fixed to the sheath so that they can share a predetermined mutual positional relation at these ends. However, substantial portions of the tubes except for the proximal and distal ends are not fixed, but extend freely. Usually these tubes have a circular cross section, and thus relatively large spaces are formed between these tubes. Therefore, when the insertion section is bent by suitably operating the angle knobs, one or more tubes might move relatively largely. Then, the tubes might resist the smooth bending movement of the insertion section, and the distal end of the insertion section might be bent in a direction which is different from a desired direction. Apparently, this causes problem in handling the endoscope during the inspection.

In order to utilize the above endoscope sheath in a proper condition, it is necessary to pay proper consideration for an accommodation and maintenance method of the endoscope sheath or the like. To this end, there has been proposed means shown in, for example, U.S. Pat. No. 4,997,084. This means concerns a method of packaging an endoscope sheath, and more particularly, a bag capable of accommodating the sheath by a holder having a larger diameter than an aperture of the endoscope sheath in a straight condition.

In this prior packaging method, however, there are various defects. That is, the endoscope sheath is constructed by combining a long channel and a plurality of tube members in view of construction, so that if the insertion sheath sections of the endoscope are accommodated so as to overlap themselves in case of accommodating the endoscope sheath in a package having a spiral recess, or if the long channel is accommodated while remaining cross-sectional shape of the channel at the time of usage, the overlapped sheath portions are increased in volume. Then, it is necessary to increase the height of the package itself, so that the package has to be large.

As described above, since the endoscope sheath is, generally, of disposal, in a large hospital or clinics having a large number of patients, a large number of endoscope sheaths must be prepared. Then, in the case of the large package, even if a great number of large packages are overlapped one on the other for reserving, a large or wide reserving space must be provided.

In order to avoid the above described large reserving space, there has been provided a method in which the long insertion sheath is spirally wound in turn to accommodate it in the package. In this way, when the insertion sheath section is spirally wound, a lumen such as an endoscope insertion channel formed in the insertion sheath is kinked and remains in the kinked condition or the lumen is subjected to an unexpected injury, or when the endoscope is inserted into the endoscope insertion channel of the insertion sheath, the insertion sheath is broken, so that when the insertion sheath is combined with the endoscope for the usage in the medical operation field, interference arises.

SUMMARY OF THE INVENTION

It is an object of the present invention to eliminate the above described disadvantages of the conventional package for packaging the endoscope sheath.

It is another object of the present invention to provide a package for packaging an endoscope sheath, in which an endoscope sheath for covering the endoscope is accommodated properly and compactly, thereby realizing a reduction in the size of the package.

According to a first aspect of the present invention, there is shown a package assembly for packaging an endoscope cover for covering the outer surface of the endoscope comprising a cover for an insertion tube section of the endoscope, and a package base member for accommodating the endoscope cover therein, the cover section is accommodated in the package base member so as not to overlap itself, under the state of packaging.

According to a second aspect of the present invention, there is shown a package assembly for packaging an endoscope cover for covering the outer surface of the endoscope comprising a cover for an insertion tube section of the endoscope, a package base member for accommodating the endoscope cover therein, and means, for accommodating other components, which is placed at the inner portion of the package base member surrounded by the cover of the insertion tube section of the endoscope cover spirally wound along the periphery of the package base member.

According to a third aspect of the present invention, there is shown a package assembly for packaging an endoscope cover for covering the outer surface of the endoscope comprising a cover for an insertion tube section of the endoscope, a package base member for accommodating the endoscope cover therein, and a suction tube at its proximal end thereof, the cover of the insertion tube section of the endoscope cover and the suction tube at its proximal end thereof are spirally wound and overlapped, respectively, under the state of packaging.

According to a fourth aspect of the present invention, there is shown a package assembly for packaging an endoscope cover for covering the outer surface of the endoscope comprising a cover for an insertion tube section of the endoscope, and a package base member for accommodating the endoscope cover therein, the overlapped insertion tube cover section accommodated in the package base member being thinner than the thickest portion of the endoscope cover, under the state of packaging.

The cover of the insertion tube section of the endoscope cover and the suction tube at its proximal end are spirally wound and overlapped, respectively, with a porous sheet intervened therebetween. The suction tube at its proximal end is placed at the center portion of the spirally wound insertion tube cover section.

According to the present invention, there is shown a package assembly for packaging an endoscope cover for covering the outer surface of the endoscope comprising a cover for an insertion tube section of the endoscope, and a package base member for accommodating the endoscope cover therein, the cover of the insertion tube section of the endoscope cover being accommodated in the package in the folded or meander state under the state of packaging, and a channel provided in the cover for an insertion tube section of the endoscope and for inserting the endoscope body being crushed to decrease the volume of the insertion tube section cover in the radial direction.

BRIEF DESCRIPTION OF THE DRAWINGS

FIG. 1 is a perspective view showing an endoscope system of first embodiment of a package according to the present invention;

FIG. 2 is a cross-sectional view showing an insertion sheath of an endoscope;

FIG. 3 is a perspective view showing a package for packaging an endoscope sheath in which a sheath for covering an endoscope is accommodated;

FIG. 4 is a perspective view showing a second embodiment of a package for packaging an endoscope sheath according to the present invention in which a sheath for covering an endoscope is accommodated;

FIGS. 7a and 7b are explanatory views showing a relation between an opening portion and a tong portion which are formed in a base member of the package;

FIG. 8 is a perspective view showing a fourth embodiment of a package for packaging an endoscope sheath according to the present invention in which a sheath for covering an endoscope is accommodated;

FIG. 9 is a perspective view showing a fifth embodiment of a package for packaging an endoscope sheath according to the present invention in which a sheath for covering an endoscope is accommodated;

FIGS. 10a and 10b are perspective views showing a sixth embodiment of a package for packaging an endoscope sheath according to the present invention in which a sheath for covering an endoscope is accommodated;

FIG. 11 is a perspective view showing a seventh embodiment of a package for packaging an endoscope sheath according to the present invention in which a sheath for covering an endoscope is accommodated;

FIG. 12 is a partial sectional view showing the package shown in FIG. 11;

FIG. 13a and 13b are cross-sectional views showing an altered state of the insertion sheath of the endoscope;

FIG. 14 is a perspective view showing a eighth embodiment of a package for packaging an endoscope sheath according to the present invention;

FIG. 15 is a perspective view showing a ninth embodiment of a package for packaging an endoscope sheath according to the present invention in which a sheath for covering an endoscope is accommodated;

FIG. 16 is an enlarged side view showing pins for holding the endoscope insertion sheath;

FIG. 17 is a perspective view showing a tenth embodiment of a package for packaging an endoscope sheath according to the present invention in which a sheath for covering an endoscope is accommodated;

FIG. 18 is a cross-sectional view showing the package shown in FIG. 17 taken along line 18—18;

FIG. 19 is an explanatory view showing a relation of various sizes of packages for accommodating insertion sheaths having different lengths;

FIG. 21 is a cross-sectional view showing the package shown in FIG. 20 taken along line 21—21;

FIG. 22 is a perspective view showing a state in which a package with the insertion sheath accommodated therein is put in a bag;

FIG. 23 is a perspective view showing a twelve embodiment of a package for packaging an endoscope sheath according to the present invention in which a sheath for covering an endoscope is accommodated;

FIG. 24 is a perspective view showing a thirteen embodiment of a package for packaging an endoscope sheath according to the present invention in which a sheath for covering an endoscope is accommodated; and FIG. 25 is a cross-sectional view showing the package shown in FIG. 24 taken along line 25—25.

PREFERRED EMBODIMENT OF THE INVENTION

Figure 5:
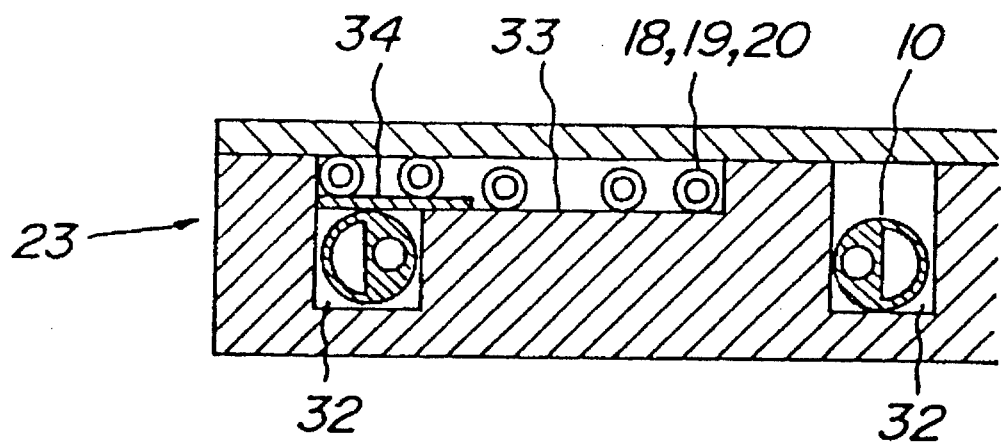
FIG. 5 is a cross-sectional view showing the package shown in FIG. 4 taken along line 5—5.

Referring to the drawings, a package for packaging an insertion tubular section of an endoscope system according to the present invention is explained. FIGS. 1 to 3 show a first embodiment of a package for packaging an insertion section of an endoscope sheath. FIG. 1 is a perspective view showing an entire endoscope system in which an endoscope insertion sheath (hereinafter, referred to as a sheath) with channels formed therein is attached. There is shown a cart 1 which is accommodates therein a peripheral apparatus such as a light source device 2, a video processor 3, a fluid control device 4, an extender for an endoscope sheath with channels formed therein 5 (hereinafter, referred to as an extender), and a monitor 6 or the like. The light source 1 is connected to an endoscope 7 for use in an endoscope insertion sheath with channels formed therein (hereinafter, referred to as an endoscope to be covered). The endoscope 7 to be covered is connected to a cable 8 for supplying signals obtained from an imaging element (not shown) provided near a distal end of an insertion port of the endoscope 7 to the video processor 3. The endoscope 7 is, also, covered by a cover 9. This cover 9 comprises an insertion sheath portion 10, an operation section sheath portion 11, and a universal sheath portion 12. This cover 9 attaches the insertion sheath portion 10 to the endoscope to be covered 7 through a cover holding means 13 for holding the cover 9.

The extender 5 is provided with an extender tube 14.

FIG. 2 is a cross-sectional view showing the insertion sheath portion 10. The insertion sheath portion 10 has formed therein an endoscope insertion channel 15 in which an insertion section of an endoscope is inserted, a forceps insertion channel 16, and an air feeding and water feeding channel 17. The insertion sheath portion 10 is connected to a proximal end suction tube 18 communicated to the forceps insertion channel 16, an air feeding tube 19 communicating to the air feeding and water feeding channel 17, and a water feeding tube 20.

Proximal end suction tube 18, air feeding tube 19, and water feeding tube 20 are connected to a suction apparatus, an air feeding apparatus, and a water feeding apparatus which are not shown, through the fluid control device 4 shown in FIG. 1, respectively.

At the proximal end of the insertion sheath portion 10, there is provided an endoscope operation member fixing coupling opening member 21 for fixing the insertion sheath portion 10 to the operation section of the endoscope (not shown). This opening member 21 is formed with an opening member 22 for fixing the operation section of the endoscope which is branched from the forceps insertion channel 16 of the insertion sheath portion 10.

In this embodiment, the opening members 21 and 22 are formed by a resin instead of metal.

FIG. 3 is a perspective view showing a package in which respective members such as the insertion sheath portion 10, the operation section sheath portion 11, the universal sheath portion 12, a disposable angle knob 24, a disposable mouth piece 25, an angle knob cover (not shown), cover for the cover holding member(not shown) or the like which are used in the case of endoscope observation, are accommodated in a package 23 for the cover, and a lid for the package is opened. The package 23 comprises a base member 26 and a lid member 27, and these members are formed by high polymer material or paper having gas permeable porous of diameter of 0.2 μm in which at least one portion of pores is gas permeable and any kinds of bacilli are not passed. Also, the base member 26 and the lid member 27 are covered by a film member 28 which has gas permeable porous of diameter of at most 0.2 μm in which at least one portion of pores is gas permeable and any kinds of bacilli are not passed.

The base member 26 is then provided with a first spiral recess 29 formed in such a manner that each portions of the insertion sheath portion 10 do not overlap and are fixed while spirally winding. The insertion sheath portion 10 is accommodated in this recess 29 by fitting it thereinto. Inside of the first recess 29 for fitting the insertion sheath portion 10 thereinto, a second recess 30 for accommodating the proximal end suction tube 18, the air feeding tube 19, and the water feeding tube 20 is provided and the proximal end suction tube 18 is wound in the same direction as that of the insertion sheath portion 10 accommodated in the second recess 30.

A space 31 approximate the first and the second recesses 29,30 at the inner side of the base member 26 is provided with an recess for accommodating respective members such as operation section sheath portion 11 or the like for use simultaneously in the case of endoscope observation and these respective members are accommodated in this recess.

The above universal sheath portion 12 is accommodated in the folded state and the thickness of the folded sheath portion 12 is made thinner than the maximum diameter of the endoscope operation member fixing coupling opening member 21.

In this way, after respective members are accommodated in the package 23, the members are sterilized with gas and shipped and transferred to users. Usually, tens of packages in which the endoscope sheath is packaged, respectively, are packaged by a corrugated cardboard as a set and transferred. In this case, it is convenience for user to indicate the contents such as kinds and size of the sheath to the package or the corrugated cardboard. If a plurality of packages are accommodated in the corrugated cardboard, the packages can be gas-sterilized as it is.

As described above, according to the present embodiment, the insertion sheath portion 10 of the cover 9 can be accommodated in the package 23 in the two dimension fashion without stacking with each other, so that the thickness of the package 23 can be remained within a minimum limit. The insertion sheath portion 10 and the the proximal end suction tube 18 or the like are concentrically wound in the same direction, so that the space can be efficiently utilized and thus the package 23 can be reduced in size. Other necessary members can be accommodated in a residue space 31 other than the space in which the insertion sheath portion 10 or the like are spirally wound, so that the space in the package 23 can be effectively utilized.

Since the proximal end suction tube 18 or the like are wound at the inner side of the base member 26 of the package 23, the insertion sheath portion 10 is comparatively loose-wound at the outer side thereof, and thus a tendency to kink of the insertion sheath portion which becomes troublesome in the case of endoscope usage, can be prevented.

At least a part of the base member 26 and the lid member 27 of the package 23 is formed by a high polymer substance or a paper having a property in which at least one portion of pores is gas permeable and any kinds of bacilli are not passed, so that sterilization efficiency becomes increased, since the package can be sterilized by gas sterilization. The base member 26 and the lid member 27 of the package 23 is covered with the film member 28 in which at least one portion of pores is gas permeable and any kinds of bacilli are not passed without gap, so that gas sterilization can be performed at the package site, and thus the insertion sheath portion can be held in the sterilized condition until the package 23 is opened, so that the cover 9 can be properly held. That is, the cover 9 is shielded for bacteria.

FIGS. 4 and 5 show a second embodiment according to the present invention (FIG. 5 is a cross-sectional view taken along line 5—5 shown in FIG. 4), so that the corresponding portions thereof are labeled with the same reference number(the same is applied to following embodiments). In this embodiment, the package 23 is provided with a first recess 32 for accommodating the insertion sheath portion 10 of the endoscope therein, and is provided with a second recess 33 for accommodating the proximal end suction tube 18 or the like in such a manner that it is overlapped on the first recess 32 at the part thereof.

Also, the depth of the recess 33 is defined in such a manner that it is substantially equal to the outer diameter of the endoscope operation member fixing coupling opening member 21 and it does not become deeper than the outer diameter of the endoscope operation member fixing coupling opening member 21 even at the place in which it does not overlap the second recess 33. The second recess 33 is formed at the site other than the site in which the endoscope operation member fixing coupling opening member 21 having the largest outer diameter of the cover is placed, and its depth is defined to make it substantially equal to the outer most diameter of the proximal end suction tube 18, the air feeding tube 19, and the water feeding tube 20.

The insertion sheath portion 10 and the proximal end suction tube 18 or the like are accommodated in the thus formed first recess 32 and the second recess 33, respectively and in this case, a sheet having gas permeable is arranged and intervened between the insertion sheath portion 10 and the proximal end suction tube 18 and at the overlapped site thereof. The other constructions are the same as that of the first embodiment, so that its detailed explanation is omitted.

As described above, the second embodiment is constructed so that the thickness of the package 23 is determined by the outer diameter of the endoscope operation member fixing coupling opening member 21. That is, the largest thickness of the members accommodated in the package 23 is the endoscope operation member fixing coupling opening member 21, since respective members are accommodated in the recess having a thickness thinner than that of the coupling opening member 21.

If the insertion sheath portion 10 of the cover is accommodated in the first recess 32, the allowance of the thickness of the insertion sheath portion 10 corresponding a narrower thickness than that of the coupling opening member 21 is formed. By accommodating the proximal end suction tube 18 having a thickness narrower than the insertion sheath portion 18 in the allowance thickness portion, the space in the package can be effectively utilized, so that the size of the longitudinal and transversal directions of the package 23 can be made compact without increasing the thickness of the package 23.

Since the gas permeable sheet 34 is arranged between the insertion sheath portion 10 and the proximal end suction tube 18 or the like, it can be prevented to arise non-sterilized portion in the case of performing gas sterilizing.

Figure 6:
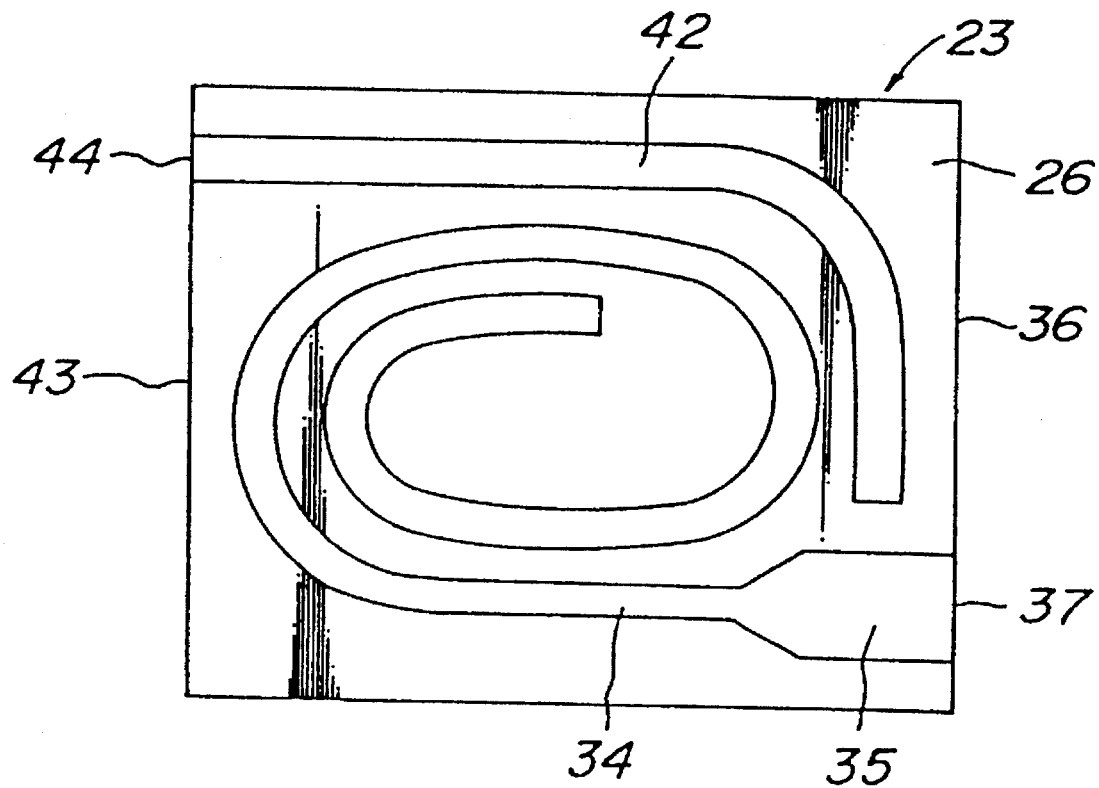
FIG. 6 is a plan view showing a third embodiment of a package for packaging an endoscope sheath according to the present invention in which a sheath for covering an endoscope is accommodated.

FIGS. 6, 7a and 7b show a third embodiment of the present invention. In this embodiment, as shown in FIG. 6 in plan view, the package has a first recess 34 for accommodating the insertion sheath portion 10 in the base member 26 of the package 23 in the spiral wound form, and the outside end portion of the recess 34 serves as an accommodating portion 35 of the endoscope operation member fixing coupling opening member 21. The accommodating portion 35 of the endoscope operation member fixing coupling opening member 21 is defined to be deeper than the depth of the first recess 34, and the end portion of the accommodating portion 35 is formed so as to make a coplanar as that of the surface of the side wall 36 of the base member 23, that is, first opening portion 37.

The first opening portion 37 is closed by a tongue portion 39 formed to a lid member 38 as shown in FIG. 7(a) by a perspective view, so as to hold and close a band-shaped gap 40 at outer periphery of the first opening portion 37 as shown in FIG. 7(b) by a perspective view. The tongue portion 39 is provided with a handle member 41, so that the first opening portion 37 can be opened by keeping it in such a manner that the handle member 41 is lifted up as shown in FIG. 7(b).

As shown in FIG. 6, the base member 26 is provided with a second recess 42 formed at the outside of the first recess 34, and for accommodating another tube used simultaneously with the insertion sheath portion 10. The end portion of the second recess 42 is formed so as to make a coplanar as that of the surface of the side wall 43 of the other base member corresponding to the side wall 36 of the base member, and is used as a second opening portion 44. The second opening portion 44 is also closed by an openable and closable tongue member (not shown) as in the first opening member 37. The other construction of the package is the same as that of the first embodiment, so that its detailed explanation is omitted.

According to the present embodiment constructed as describer above, the sheath can be accommodated in the package 23 with excellent space efficiency and the sheath can be taken out without touching the other portion of the cover carelessly by drawing out the endoscope operation member fixing coupling opening member 21 by lifting up the lid member 38 in case of taking out the insertion sheath portion 10 from the package 23 and thus it is advantageous in sanitary.

At the same time, the same effect can be expected as to the other tube accommodated in the second recess 42.

FIG. 8 shows a fourth embodiment of the present invention. In this embodiment, the package comprises a first straight recess 45 for accommodating the insertion sheath portion 10 straightly and a second recess 46 formed along the extended direction of the first recess 45 and for accommodating the proximal end suction tube 18 or the like while folding it in the plane direction. The other construction is the same as that of the first embodiment, so that is detailed explanation is omitted.

According to the construction as described above, the insertion sheath portion 10 can be accommodated plainly without overlapping, and thus the thickness of the package 23 can be made minimum as well as provide that the insertion sheath portion 10 is not folded so that it is prevented from kinking in the inner channel.

FIG. 9 shows a fifth embodiment of the present invention. In this embodiment, both a first recess 45 and a second recess 46 are formed in the base member 26 of the package 23 in a meander shape in such a manner that the insertion sheath portion 10 is accommodated in and along the first recess 45 and the proximal end suction tube 18 is accommodated in and along the second recess 46. The other construction is the same as that of the first embodiment so that its detailed explanation is omitted.

According to the above construction, the insertion sheath portion 10 can be accommodated two dimensionally without overlapping, and thus the thickness of the package 23 can be minimized and a part of the insertion sheath portion 10 can evenly be accommodated while folding so that the length of package 23 can be prevented from being large even by using a long insertion sheath portion.

FIG. 10 shows a sixth embodiment of the present invention. In this embodiment, the base member 26 of the package 23 is provided with a recess 47 in such a manner that the insertion sheath portion 10 is accommodated in the recess 47 in the required direction while bending. FIG. 10(a) shows a state that the endoscope operation member fixing coupling opening member 21 is placed and accommodated at the inner end portion of the spirally wound recess 47, and FIG. 10(b) shows a state that the endoscope operation member fixing coupling opening member 21 is placed and accommodated at the outer end portion of the spirally wound recess 47. The other construction is the same as that of the first embodiment so that its detailed explanation is omitted.

According to the above construction, the insertion sheath portion 10 can be accommodated two dimensionally without overlapping, and the accommodating state of the insertion sheath portion 10 can be optionally changed, for example, if the distal end portion of the insertion sheath portion 10 is not intended to be bent, the insertion sheath portion 10 can be accommodated as shown in FIG. 10(a), and if the proximal end portion of the insertion sheath portion 10 is not intended to be bent, the insertion sheath portion 10 can be accommodated as shown in FIG. 10(b).

FIG. 11 shows a seventh embodiment of the present invention. This embodiment shows a state that a lid of a package 54 having a recess 53 formed therein for fixing the insertion sheath portion 10 while spirally winding, is opened. The package 54 has a base member 55 and a lid member 56, and these members are formed by high polymer material or paper having gas permeable porous of diameter of 0.2 μm in which at least one portion of pores is gas permeable and any kinds of bacilli are not passed. Also, the base member 55 and the lid member 56 are covered without any gaps with a film member 57 which has gas permeable porous of diameter of at most 0.2 μm in which at least one portion of pores is gas permeable and any kinds of bacilli are not passed.

FIG. 12 shows a cross-sectional view of a part of the base member 55 and the lid member 56. As shown in FIG. 12, a porous sheet 59 having gas permeability is fixed onto a wall portion 55a of the channel 53 formed on the base member 55 and a recess 56a formed at the site of the lid member 56 corresponding to the recess 53.

At least one of the base member 55 and the lid member 56 is provided with a ventilating hole so as to lead atmosphere in the porous sheet 59, thereby surely reaching a sterilizing gas in the case of sterilization to the insertion sheath portion 10. In this embodiment, the base member 55 and the lid member 56 are provided with ventilating holes 60, 61, respectively.

FIGS. 13a and 13b show a cross-section of the insertion sheath portion 10 accommodated in the package. That is, FIG. 13(a) shows a state of the insertion sheath portion 10 being in a substantially circular state before accommodating it in the package, and then, an endoscope insertion channel 62, a forceps channel 64 and a water feeding channel 65 which are surrounded by a thick wall portion 63 and FIG. 13(b) shows a state of accommodating the insertion sheath portion in the package, in this case, the endoscope insertion channel 62 is in a constricted conditions.

In this way, after the insertion sheath portion 10 is made in the constricted conditions and respective members are accommodated in the package 54, the members are sterilized with gas and shipped and transferred to users. Usually, tens of packages in which the endoscope sheath is packaged, respectively, are packaged by a corrugated cardboard as a set and transferred. In this case, it is convenience for the user to indicate the contents such as kinds and size of the cover 9 to the package or the corrugated cardboard. If a plurality of packages are accommodated in the corrugated cardboard, the packages can be gas-sterilized as it is.

As described above, according to the present invention, when the insertion sheath portion 10 is accommodated in the package 54, the endoscope insertion channel 52 can be made constricted conditions by drawing out the air in the endoscope insertion channel 52 formed in the insertion sheath portion 10 with the well known means or by adding the pressing force onto the portion of the endoscope insertion channel 52 from outside. In this way, the insertion sheath portion 10 can be fixed in a recess 53 of the base member 55 while winding the insertion sheath portion with a small R. Therefore, the recess 53 has minimum diameter and a spacing of the recess has a minimum spacing, so that the package 54 can be down-sized.

Moreover, when the insertion sheath portion 10 is utilized practically, the constricted conditions of the insertion channel can be restored to the opened conditions by the endoscope insertion portion into the endoscope insertion channel 62, so that any problem resulting from the constriction does not occur. If in addition to the endoscope insertion channel 62, the forceps channel 64 or the like are constricted, the insertion sheath portion 10 can be accommodated more compactly.

Since the porous sheet 59 is fixed around the site in which the insertion sheath portion 10 is fixed, the insertion sheath portion 10 does not contact directly with the base member 55 and the lid member 56, so that in case of sterilizing the members with gas through the ventilation hole 60, it can be prevented the insertion sheath portion having the part which is not contacted with the gas from arising.

At least a part of the base member 55 and the lid member 56 of the package 54 is formed by the high polymer material or paper having gas permeable porous in which at least one portion of pores is gas permeable and any kinds of bacilli are not passed, so that it can be sterilized with gas, thereby obtaining an excellent sterilization efficiency. Also, the base member 55 and the lid member 56 are covered without any gap by a film member 57 which has gas permeable porous in which at least one portion of pores is gas permeable and any kinds of bacilli are not passed, the package 54 can be gas-sterilized as it is and thus the package 54 can be held in the sterilized conditions until it is opened, thereby intending a preferable preservation of the cover 9.

An eighth embodiment of the present invention is shown in FIG. 14 in which the portions corresponding to the seventh embodiment are designate with the same references. In this embodiment, a recess 66 formed in the base member 55 and for fixing the insertion sheath portion 10 comprises a straight portion 66a and an R portion 66b and when the insertion sheath portion 10 is fixed in the R portion 66b, the endoscope insertion channel is made kinked. The base member 55 and the lid member 56 are formed by a material having gas permeable pores as shown in the seventh embodiment, and these base member and the lid member are covered with the film shaped member 57 having gas-permeable pores. The other construction is the same as that of the seventh embodiment so that its detailed explanation is omitted.

When the insertion sheath portion 10 is accommodated in the thus constructed package 54, it can be accommodated without the winding reliability of the distant end portion of the insertion sheath portion 10 and then the sterilization is not made at the site other than the necessary portion, so that the insertion sheath portion 10 can be inserted smoothly in the endoscope insertion channel in case of using the endoscope. The other advantageous effects are the same as that of the seventh embodiment, so that then explanation is omitted.

FIG. 15 is a perspective view showing the state in which the insertion sheath portion 10 is fixed in a base member 67 according to a ninth embodiment of the present invention. In this embodiment, a base member 66 does not comprise a recess for fixing the insertion sheath portion 10 as in the seventh embodiment, but comprises a plurality of pins 68 studded along the fixing site of the insertion sheath portion 10.

As shown in FIG. 16 by an enlarged side view, these pins 68 are fixed in such a manner that a head portion 68a is thicker than a rod portion 68b of the pin 68 so that the insertion sheath portion 10 can be forcibly inserted between the rod portions 68b.

The base member 55 and the lid member 56 are formed by a material having gas permeable pores as shown in the seventh embodiment, and covered with the film shaped member 57 having gas-permeable pores. The other construction is the same as that of the seventh embodiment so that its detailed explanation is omitted.

The ninth embodiment is constructed as described above, and then, when the insertion sheath portion 10 in the constricted conditions is fixed to the base member 55 through the pins 68, the insertion sheath portion 10 can be accommodated in the the package 54 while spirally winding with small R. Therefore, the spacing between the pins 68 can be made minimum so that down-sizing of the package 57 can be performed.

In the case of gas-sterilization of the insertion sheath portion, even if the lid member 56 does not have gas permeability, the insertion sheath portion 10 does not touch the lid member 56, so that if the gas is supplied so as to fill it between the lid member 56 and the base member 55, the insertion sheath portion 10 can be sterilized in such a manner that the whole portion of the insertion sheath portion is touched to the gas. The other advantageous effects are the same as that of the seventh embodiment, so that their explanation is omitted.

A tenth embodiment of the present invention is shown in FIGS. 2 and 17 by a cross-sectional view and a perspective view. As shown in FIG. 2, in this embodiment, a kink protection member 73 is previously inserted in the endoscope insertion channel 15 of the insertion sheath portion 10 and this insertion sheath portion is accommodated in the package 74. The kink preventing member 73 is formed by a coil of stainless steel or a rod member of silicon resin having high flexibility and not kinked, so that the kink preventing member 10 can be detachably provided in the endoscope insertion channel 15.

FIG. 17 is a perspective view showing a state in which the insertion sheath portion 10 is accommodated in a package 74 and the lid member of the package is opened. The package 74 comprises a base member 75 and a lid member 76 and formed by a paper or a plastic material capable of recycling and classified as PETP (polyethylene terephthalate) and HDPE (high-density polyethylene). The base member 75 and the lid member 76 have gas permeable porous of diameter of 0.2 μm in which at least one portion of pores is gas permeable and any kinds of bacilli are not passed. Also, the base member 75 and the lid member 76 are covered without any gaps with a film member 77 which has gas permeable porous of diameter of at most 0.2 μm in which at least one portion of pores is gas permeable and any kinds of bacilli are not passed.

The base member 75 is provided with a recess 78 formed in such a manner that the insertion sheath portion 10 is fixed in the substantially U-shaped form while having one bending portion, so that the insertion sheath portion 10 can be fixed and accommodated in the recess 78. In this case, as described above, the kink preventing members are inserted in the endoscope insertion channel or the like of the insertion sheath portion 10, respectively.

FIG. 18 is a fragmentary cross sectional view taken along line 18—18 of FIG. 17 showing a status in which the insertion sheath portion 10 is fixed and accommodated in the package 74. As shown in FIG. 18, the insertion sheath portion 10 is provided with an endoscope insertion channel 15 for inserting the endoscope insertion section, a forceps channel 16 for inserting forceps, and an air feeding and water feeding channel 17.

In this case, kink preventing member 73, 79, 80 are inserted in the endoscope insertion channel 15, the forceps channel 16, and the air feeding and water feeding channel 17, respectively, and the insertion sheath portion 10 is fixed in the recess 78 in such a manner that the endoscope insertion channel 15 is positioned inside the bending.

In this way, after the insertion sheath portion 10 is constricted and is accommodated in the package 74, the members are sterilized with gas and shipped and transferred to users. Usually, tens of packaged insertion sheath portion 10 are packaged by a corrugated fiberboard box as a set and transferred. In this case, it is convenience for user to indicate the contents such as kinds and size of the insertion sheath portion 10 to the corrugated fiberboard box or the like. If a plurality of packages 74 are accommodated in the corrugated fiberboard box, the packages can be gas-sterilized as it is.

As described above, according to this embodiment, the insertion sheath portion 10 can be accommodated compactly, so that the down-sizing of the package can be performed. While the kink preventing member 73, 79, 80 are inserted in the lumen of the insertion sheath portion 10 of the cover 9 so that even if the cover 9 is inserted in the recess 78 with small R while bending the cover, the lumen does not break out.

In this case, the kink preventing member 73 may be inserted in only the endoscope insertion channel 15 instead of in the forceps channel 16 and the air feeding and water feeding tubular channel 17 which have thick wall portion, since the endoscope insertion channel 15 is liable to subject to a deforming habit and has a large aperture, the sterilization becomes easy and thus the sterilizing treatment also becomes easy after inserting the kink preventing member which is not sterilized.

The insertion sheath portion 10 is also fixed in the recess 78 by placing the insertion sheath portion 10 inside, and the thick wall portion in which the forceps channel 16 and the air feeding and water feeding channels are provided, of the insertion sheath portion is bent with a larger R than that of the portion in which the endoscope insertion channel 15 is provided so that it is comparatively difficult to subject to the deforming habit and thus the insertion sheath portion can be prevented from affecting the operation of the endoscope in case of utilizing the endoscope.

At least a part of the base member 75 and the lid member 76 of the package 74 is formed by the paper or the high polymer in which at least one portion of pores is gas permeable and any kinds of bacilli are not passed, thereby obtaining high sterilization efficiency by gas sterilization. The base member 75 and the lid member 76 are covered without any kinds of gaps with a film member 77 in which at least one portion of pores is gas permeable and any kinds of bacilli are not passed, so that the package 74 can be gas-sterilized as it is and thus the package 74 can be held in the sterilized conditions until it is opened, thereby intending a preferable preservation of the cover 9.

While the insertion sheath portion 10 has to provide various kinds of size in accordance with the kinds of endoscope intended to use with the insertion sheath portion 10, so that different kinds of the packages 74 must be prepared according to the size of the cover 9, thereby arising a problem in preservation with the excellent space efficiency.

FIG. 19 is a perspective view of the package in which a plurality of packages 74 are provided for two kinds or over of the insertion sheath portions 10. In these packages, one package has equal height and width and minimum length as a reference and other package has equal height and width and length of integer times or so.

That is, as shown in FIG. 19, the insertion sheath portions 10a, 10b, 10c are accommodated in the three kinds of packages 74a, 74b, 74c having different length, respectively. In this way, respective packages have equal or common width W and height H and different lengths of L1, L2, and L3. Among these lengths L1, L2, and L3, there is an relation that the length of other packages is integral multiples of minimum length of L1 as a reference.

According to this construction, when a plurality of packages 74a, 74b, 74c are stacked and preserved, these packages can be stacked with high efficiency while registering the size of package.

Figure 20:
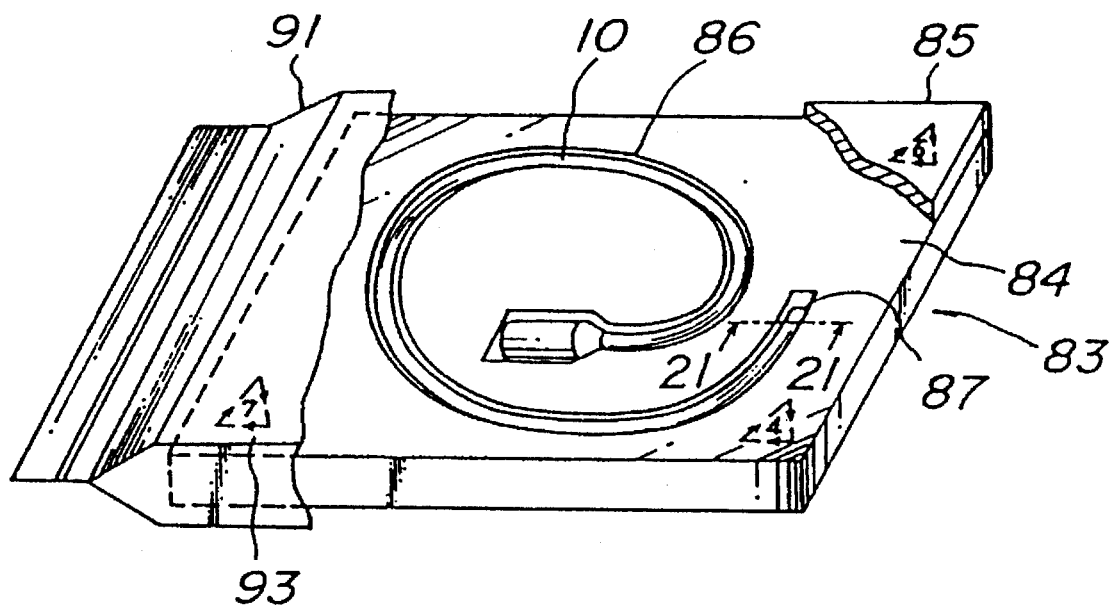
FIG. 20 is a perspective view showing an eleven embodiment of a package for packaging an endoscope sheath according to the present invention in which a sheath for covering an endoscope is accommodated.

FIG. 20 is a partially notched perspective view showing an insertion sheath portion 10 accommodated in a package 83. The package 83 has a bag 91 made of the same material as that of a base member 84 and a lid member 85 formed by a paper or a plastic material or the like capable being recycled and classified as PETP (polyethylene terephthalate) and HDPE (high-density polyethylene).

At least a part of the base member 84 and the lid member 85 of the package 83 is formed by a paper or a high polymer material having gas permeable pores of diameter of 0.2 μm or less in which at least a part of the members 84 and 85 is gas permeable and any kinds of bacilli are not passed.

The insertion sheath portion 10 is fixed in a recess 86 spirally formed in the base member 84 in such a manner that a distal end portion 87 of the insertion sheath portion 10 is placed outside. FIG. 21 is a fragmentary cross sectional view taken along lines 21—21 of FIG. 20 showing a status in which the insertion sheath portion 10 is fixed and accommodated in the package 83. As shown in FIG. 21, the distal end portion 87 of the insertion sheath portion 10 is fixed in the recess 86 in such a manner that the surfaces of the insertion sheath portion 10 corresponding to upper and lower bending directions thereof in case of combining it to the endoscope are contacted to right and left side walls 86a and 86b, respectively.

The insertion sheath portion 10 comprises an endoscope inserting channel 88 for inserting the insertion portion of the endoscope having a function in which the distal end portion of the endoscope insertion portion is bent in the upper and lower directions and right and left direction or in the upper and lower direction, and comprises a forceps insertion channel 89 for inserting the forceps and an air feeding and water feeding channel 90.

FIG. 22 is a perspective view showing a status in which after the insertion sheath portion is fixed in the base member and the base member is covered with the lid member and the whole member is inserted in a bag 91 thereby tightly closing the bag by a fastener 92. That is, the bag 91 is formed by a film shaped member having gas permeable pores of diameter of 0.2 μm or less and an openable and closable fastener 92 is provided on the inserting aperture. A symbol 93 for indicating the material is labeled on the surface of the bag. As shown in FIG. 20, similar labeling is performed on the surface of the base member 84 and the lid member 85.

In this way, after the insertion sheath portion 10 is constricted and is accommodated in the package 83, the members are sterilized with gas and shipped and transferred to users. Usually, tens of packaged insertion sheath portion 10 are packaged by a corrugated fiberboard box as a set and transferred. In this case, it is convenient for user to indicate the contents such as kinds and size of the insertion sheath portion 10 to the corrugated fiberboard box or the like. If a plurality of packages 83 are accommodated in the corrugated fiberboard box, the packages can be gas-sterilized as it is.

As described above, according to this embodiment, the insertion sheath portion 10 of the cover 9 can be accommodated compactly by spirally winding, so that the down-sizing of the package can be performed. While the winding habit of the distal end portion 87 of the spirally wound insertion sheath portion 10 is only in the upper and lower bending directions instead of in the right and left directions. Generally, the endoscope has an operating knob for performing the bending in the usual upper and lower direction in case of utilizing the endoscope, so that even having the bending habit in the upper and lower directions, this bending habit can easily be calibrated and thus the operation is not subjected to a bad effect.

When the insertion sheath portion 10 inserted in the package 83 is sterilized with gas, the sterilization is performed by opening the insertion opening of the bag 91 with the fastener and the sterilizing condition of the insertion sheath portion can be held together with the package 83 by closing the insertion opening after completion of the sterilization. In case of using the insertion sheath portion 10, when the insertion opening of the bag 91 with the fastener is opened, the insertion sheath portion 10 can easily be taken out between the base member 84 and the lid member 85 under the sterilization condition by opening the insertion opening of the bag 91 with fastener, so that the package 83 must not be disposed every time.

If the base member 84 and the lid member 85 are formed with a material of bionic degradable type or a material of combustible type, it is possible to contribute the environmental conservation, and if the base member 84 and the lid member 85 are formed with a material capable of being recycled, it is possible to contribute to the conservation of resources.

At least a part of the base member 84 and the lid member 85 of the package 83 is formed by the paper or the high polymer in which at least one portion of the members is gas permeable and any kinds of bacilli are not passed, thereby obtaining a high sterilization efficiency by gas sterilization. The base member 84 and the lid member 85 are covered without any kinds of gaps with the bag made of a film member in which at least one portion thereof is gas permeable and any kinds of bacilli are not passed, so that the package 83 can be gas-sterilized as it is and thus the package 83 can be held in the sterilized conditions until it is opened, thereby intending a preferable preservation of the insertion sheath portion 10.

FIG. 23 shows a twelfth embodiment of the present invention. In this embodiment, the elements corresponding to those of the eleventh embodiment are labeled with the same reference as that of the eleventh embodiment. The same is applied to the following embodiments. In this embodiment, a recess 86 for fixing the insertion sheath portion 10 is provided in a base member 84 of a package 83, and the insertion sheath portion 10 is fitted and fixed in the recess 86.

The insertion sheath portion 10 comprises an endoscope inserting channel 88 for inserting the insertion portion 94 of the endoscope having a function in which the distal end portion 87 of the endoscope insertion portion 94 (shown by broken lines) is bent only in the upper and lower directions, and comprises a forceps insertion channel 89 for inserting the forceps.

In this embodiment, the distal end portion 87 of the insertion sheath portion 10 is fixed in the recess 86 in such a manner that the surfaces of the insertion sheath portion 10 corresponding to upper and lower bending directions thereof face to the direction orthogonal to right and left side walls 86a and 86b, respectively. In this embodiment, also, after the insertion sheath portion 10 is fixed in the base member 84 and the base member is covered with the lid member and the whole member is inserted in a bag 91, thereby tightly closing the bag by a fastener 92. That is, the bag 91 is formed by a fight polymer having gas permeable pores and in which at least a part of the members 84 and 85 is gas permeable and any kinds of bacilli are not passed.

The other construction of the package is the same as that of the eleventh embodiment, so that its detailed explanation is omitted.

Since the twelfth embodiment of the present invention is constructed as described above, the bending habit of the distal end portion 87 of the insertion sheath portion 10 is only in the direction orthogonal to the upper and lower bending direction instead of in the upper and lower direction. Therefore, the bending section of the endoscope having bending function only in the upper and lower direction is not bent in the right and left direction even by adding external force, so that, in case of using the endoscope by combining the insertion sheath portion 10 to the endoscope, the bending habit provided to the insertion sheath portion 10 can be calibrated naturally, thereby obtaining a preferable operation.

The base member or the like is accommodated in the bag 91 formed by a high polymer in which at least one portion of the bag is gas permeable and any kinds of bacilli are not passed, so that the base member or the like can be gas-sterilized as it is and the sterilization working can easily be performed. The other advantageous effects besides the above described effect are the same as those of the eleventh embodiment, so that their detailed explanation is omitted.

FIGS. 24 and 25 (cross-sectional view taken along line 25—25 of FIG. 24) show a thirteenth embodiment of the present invention. This embodiment provides a package 83 capable of accommodating various different sizes of length of the insertion sheath portion 10 or various different sizes of the endoscope inserting channel. FIG. 24 shows a package 83 in which a short insertion sheath portion 10 is accommodated, so that a part of the recess 86 becomes vacant, that is, the rest portion 86c thereof is provided.

In this way, the package according to this embodiment may accommodate various kinds of the insertion sheath portion 10, so that the type and name or the like of the endoscope intended to be used together with the insertion sheath portion 10 are labeled on the surface of the bag 91. The other construction of the package is the same as that of the eleventh embodiment, so that its detailed explanation is omitted.

The present embodiment is constructed as described above, and can be utilized together with the same type of the package 83 in common, so that the arrangement of the package 83 becomes easy and the package 83 itself can be manufactured with mass production at a cheap price. In the package 83, also, information of types of used endoscope and the insertion sheath portion 10 are displayed on the surface of the package 83, so that it can be prevented to open the other package 83 in error. The other advantageous effects other than the above described effect are the same as those of the eleventh embodiment, so that their detailed explanation is omitted.

What is claimed is:

1. A packaged endoscope cover assembly comprising:
   (a) an endoscope cover comprising:
      (i) a flexible, elongated, thin-walled tubular cover section for covering an insertion tube section of an elongated, flexible endoscope therein and for insertion into a body cavity of a patient,
      (ii) a coupling section, connected to said tubular cover section, for coupling said tubular cover section to a body of the endoscope, and
      (iii) a tubular portion extending from the coupling section; and
   (b) a package comprising:
      (i) a first portion for accommodating said coupling section,
      (ii) a second portion for accommodating said tubular cover section and being constructed so as to be folded back with respect to said first portion accommodating the coupling section, and
      (iii) a third portion for accommodating the tubular cover section in a substantially straight configuration.

2. An assembly as claimed in claim 1, wherein the second accommodating section has a substantially straight configuration.

3. An assembly as claimed in claim 1, wherein the first portion further comprises a plurality of portions bent with specified curvatures.

4. An assembly as claimed in claim 1, wherein the first portion is formed in a meander configuration.

5. An assembly as claimed in claim 1, further comprising a cover member for covering said package section.

6. An assembly as claimed in claim 1, wherein an outer surface of said endoscope cover is substantially flush with an outer surface of said package and said assembly further comprises a lid layer disposed on said outer surface of said package.

7. An assembly as claimed in claim 4, wherein a distance between a first end of said first portion having a meander configuration and a second end of said first portion is substantially equal to a length of said second portion for accommodating the cover section in a substantially straight configuration.

8. The packaged endoscope cover assembly as in claim 1, wherein said first, second and third portions are in communication with one another.

* * * * *